United States Patent
Romesberg

(10) Patent No.: US 7,266,175 B1
(45) Date of Patent: Sep. 4, 2007

(54) PLANNING METHOD FOR RADIATION THERAPY

(75) Inventor: Merle Romesberg, Pittsburgh, PA (US)

(73) Assignee: NOMOS Corporation, Cranberry Township, PA (US)

( * ) Notice: Subject to any disclaimer, the term of this patent is extended or adjusted under 35 U.S.C. 154(b) by 188 days.

(21) Appl. No.: 10/887,966

(22) Filed: Jul. 9, 2004

Related U.S. Application Data

(60) Provisional application No. 60/487,067, filed on Jul. 11, 2003.

(51) Int. Cl.
*A61N 5/10* (2006.01)

(52) U.S. Cl. ........................................................ 378/65

(58) Field of Classification Search ................ 378/64, 378/65, 108, 151
See application file for complete search history.

(56) References Cited

U.S. PATENT DOCUMENTS

| | | | |
|---|---|---|---|
| 3,861,807 A | 1/1975 | Lescrenier et al. | |
| 3,987,281 A | 10/1976 | Hodes et al. | |
| 4,455,609 A | 6/1984 | Inamura et al. | |
| 5,373,844 A | 12/1994 | Smith et al. | |
| 5,511,549 A | 4/1996 | Legg et al. | |
| 5,596,619 A | 1/1997 | Carol | |
| 5,802,136 A | 9/1998 | Carol | |
| 6,038,283 A * | 3/2000 | Carol et al. | 378/65 |
| 6,240,162 B1 * | 5/2001 | Hernandez-Guerra et al. | 378/65 |
| 6,260,005 B1 * | 7/2001 | Yang et al. | 703/11 |
| 6,360,116 B1 | 3/2002 | Jackson et al. | |
| 6,393,096 B1 | 5/2002 | Carol et al. | |
| 6,411,675 B1 * | 6/2002 | Llacer | 378/65 |
| 6,435,717 B1 | 8/2002 | Koehler et al. | |
| 6,546,073 B1 * | 4/2003 | Lee | 378/65 |
| 6,560,311 B1 | 5/2003 | Shepard et al. | |
| 6,661,872 B2 * | 12/2003 | Bova | 378/65 |
| 2002/0006182 A1 * | 1/2002 | Kim et al. | 378/65 |
| 2002/0051513 A1 * | 5/2002 | Pugachev et al. | 378/65 |
| 2002/0080915 A1 | 6/2002 | Frohlich et al. | |
| 2002/0122530 A1 | 9/2002 | Erbel et al. | |
| 2003/0026384 A1 * | 2/2003 | Hernandez-Guerra | 378/65 |
| 2003/0048869 A1 * | 3/2003 | Stienberg | 378/65 |

(Continued)

FOREIGN PATENT DOCUMENTS

EP 0911065 A 4/1999

(Continued)

OTHER PUBLICATIONS

Pirzkall, Andrea, et al., "Comparison of Intensity-Modulated Radiotherapy with Convention Conformal Radiotherapy for Complex-Shaped Tumors," Jul. 2000, International Journal of Radiation Oncology Biology Physics, vol. 48, No. 5, pp. 1371-1380.*

(Continued)

*Primary Examiner*—Edward J. Glick
*Assistant Examiner*—Anastasia S. Midkiff
(74) *Attorney, Agent, or Firm*—Bracewell & Giuliani LLP

(57) ABSTRACT

Method and apparatus for controlling the correlation between the factors of treatment plan efficiency and dosimetric fitness to optimize the radiation therapy, or radiotherapy plan, include providing user control of the segment count, user control of total monitor units, and selection of an optimization algorithm as a method of controlling treatment efficiency.

20 Claims, 5 Drawing Sheets

U.S. PATENT DOCUMENTS

2004/0138556 A1    7/2004    Cosman

FOREIGN PATENT DOCUMENTS

EP             1041918      11/2000
WO      WO 02/49044 A2      6/2002
WO         WO0249044    *  6/2002

OTHER PUBLICATIONS

M. Romesberg, paper entitled "Controlling the tradeoff between delivery efficiency and dosimetric fitness in IMRT," presented at 44th Annual Meeting of the American Association of Physicists in Medicine (AAPM), Montreal, Jul. 14-18, 2002.

* cited by examiner (Efficiency becomes more important from top to bottom):

Dosimetric Cost = 0.453
Segment Count = 97

Dosimetric Cost = 0.653
Segment Count = 37

Dosimetric Cost = 1.26
Segment Count = 5

(Efficiency becomes more important from top to bottom):

Dosimetric Cost = 0.132
Total Monitor Units = 22365

Dosimetric Cost = 0.149
Total Monitor Units = 15624

Dosimetric Cost = 1.94
Total Monitor Units = 6640

Annealing
Dosimetric Cost = 0.131
(notice target conformality)
22365 Monitor Units

Gradient Descent
Dosimetric Cost = 0.463
10100 Monitor Units

PLANNING METHOD FOR RADIATION THERAPY

RELATED APPLICATION

This application claims the benefit of U.S. Provisional Patent Application Ser. No. 60/487,067, filed Jul. 11, 2003.

BACKGROUND OF THE INVENTION

Field of the Invention

Traditional inverse intensity modulated radiation therapy ("IMRT") planning systems attempt to find radiation intensity maps resulting in the best calculated dose distribution for a specific tumor for a specific patient. For many treatment plans, the resultant intensity maps often cannot be efficiently delivered by the radiation therapy treatment equipment, typically a conventional linear accelerator provided with a multileaf, or multiple leaf, collimator ("MLC"). Inefficient intensity maps may require a large number of monitor units ("MU") or a large number of "MLC" segments for delivery. These inefficient treatment plans, or solutions, are undesirable because they might require a large amount of delivery time, radiation beam on time, and/or radiation leakage dose to the patient. It is also undesirable to uniformly preclude the discovery of less efficient treatment plans, which may also be dosimetrically superior plans. Thus, it would be desirable to provide user control of the tradeoff, or correlation, between the factors of treatment plan efficiency and dosimetric fitness to optimize a radiation therapy, or radiotherapy, plan.

SUMMARY OF THE INVENTION

Several methods for enabling user control of the tradeoff between dosimetric fitness and delivery efficiency are being proposed. First, providing user control of the segment count in a treatment plan is proposed, wherein a delivery cost term based upon the complexity of the intensity maps may be utilized. This cost term drives the optimizer toward a simpler, more efficient solution. A second method for providing user control in a treatment plan provides user control of total monitor units. The acceptable inflation, or increase, of total monitor units is limited as the optimizer progresses from simple, efficient treatment plans toward more complex treatment plans. A third method includes choosing an optimization algorithm as a method of controlling treatment efficiency. Specifically, gradient descent and simulated annealing are compared in terms of dosimetric cost and delivery efficiency. For each of the three proposed methods, tradeoffs between dosimetric cost, segmentation count, and total MU may be compared.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification.

DETAILED DESCRIPTION OF THE INVENTION

Figure 1:
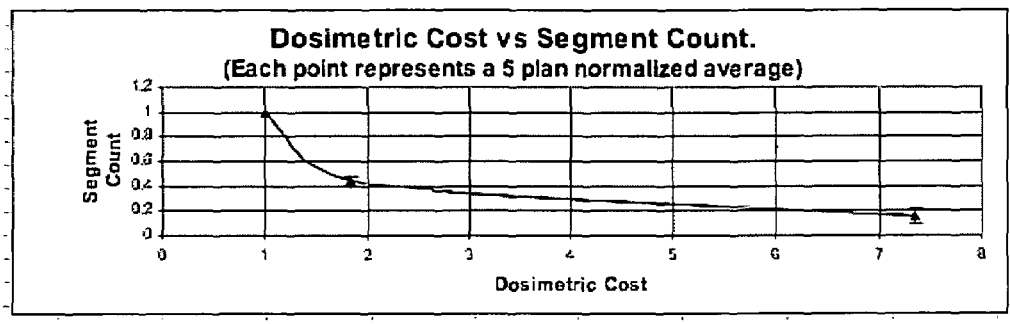
FIG. 1 is a chart illustrating the correlation between segment count and dosimetric cost in a radiotherapy plan.

In controlling the tradeoff between delivery efficiency and dosimetric fitness in radiation treatment plans, it is necessary to provide quantitative measures of delivery efficiency and dosimetric fitness of a treatment plan. "Delivery Efficiency" may be defined and quantified in terms of "Segmentation Count" and "Total Monitor Units." For multileaf collimation, or collimator, treatment plans, radiation therapy treatment involves delivering radiation in a series of shaped segments, and treatment time and delivery efficiency are proportional to the number of required segments, which is the Segment Count or Segmentation Count. For some treatment plans, such as those provided with a binary temporal modulator multileaf collimator, such as that sold by NOMOS Corporation under the trademark MIMIC®, treatment time is controlled by the total radiation beam on time of the linear accelerator used in providing the treatment, which is the Total Monitor Units. Beam on time is proportional to Total Monitor Units required for treatment delivery. As an example, for radiation treatment plans provided with a MIMIC® MLC, Total Monitor Units are a quantitative measure of Delivery Efficiency.

Dosimetric Fitness may be quantified with reference to "Dosimetric Cost." For Dosimetric Cost in an inverse IMRT treatment planning system, the fitness of a dose distribution is typically quantified by using a dosimetric cost function. Dose distributions with low Dosimetric Cost are generally deemed superior to those with a high Dosimetric Cost.

All three methods for controlling the tradeoff between Delivery Efficiency and Dosimetric Fitness are evaluated and compared in connection with a clinical radiotherapy plan. The first method of providing the desired user control comprises controlling Segment Count by use of a delivery cost term. A delivery cost term is assigned to an intensity map based upon the complexity of the intensity map. Maps with more intensity changes generally require more segments to deliver, and thus are assigned a larger delivery cost term. Simulated annealing is used as the computational method to find the solution with the best Dosimetric Cost. Solutions with a delivery cost exceeding some real valued threshold, as set by the user, are not considered. As hereinafter described, this method was evaluated on a series of MLC treatment plans, whereby Delivery Efficiency is related to Segmentation Count.

The second method comprises limiting the number of Total Monitor Units (MU) in the optimization of the treatment plan. The acceptable inflation, or increase, of Total Monitor Units is limited as simulated annealing progresses from initially simple and efficient treatment plans to more complex, and less efficient, treatment plans. A real valued threshold, as set by the user, is used to rule out, or exclude, solutions requiring an excessive number of monitor units. As hereinafter described, this method was evaluated on a series of MIMIC® MLC plans, whereby Delivery Efficiency is related to Total Monitor Units. The third method comprises controlling Delivery Efficiency by the choice of the optimization algorithm. The choice of the optimization algorithm controls the tradeoff between Delivery Efficiency and Dosimetric Fitness. A comparison is made between simulated annealing and gradient descent, in terms of Delivery Efficiency and Dosimetric Fitness. As will be herein described in greater detail, this method was evaluated on a series of MLC and MIMIC® treatment plans. For each method, a comparison is made of relevant numbers quantifying Delivery Efficiency and Dosimetric Fitness. The Segmentation Count and Total Monitor Units are used to quantify Delivery Efficiency, and a dose volume histogram ("DVH") based upon a cost function may be used to quantify Dosimetric Fitness.

Figure 2A:
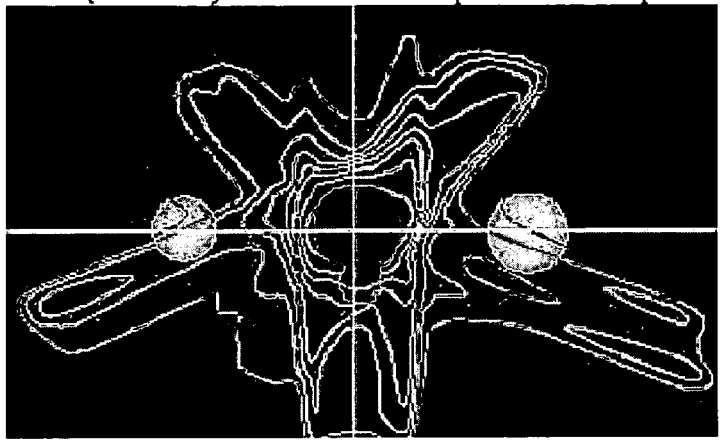
FIGS. 2A-2C are dose distribution intensity maps for three different radiotherapy plans.
Figure 2B:
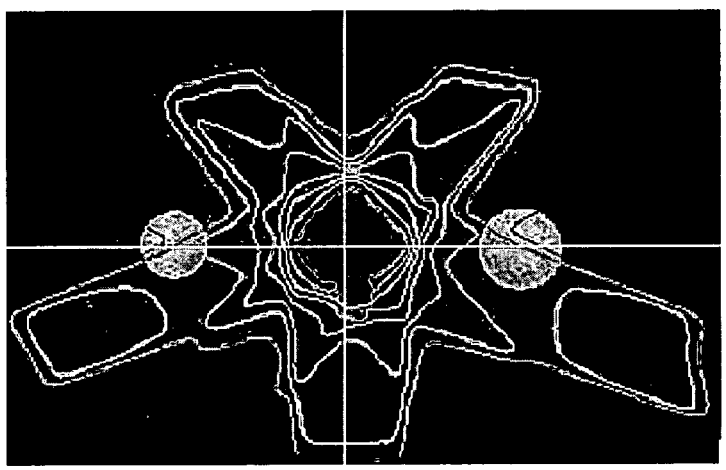
Figure 2C:
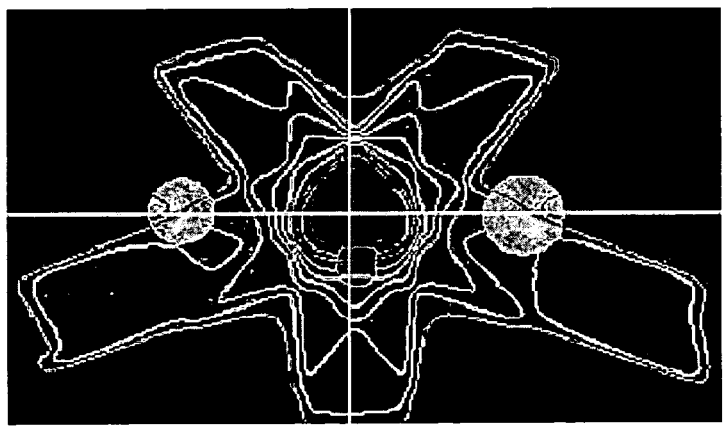

As shown in FIG. 1, the tradeoff, or correlation, between Segment, or Segmentation, Count and Dosimetric Cost for the first method is illustrated. Each point on the chart of FIG. 1 represents the average normalized Dosimetric Cost and Segmentation Count of 5 MLC plans. The Segmentation Count for the MLC based treatment plans, as seen in FIG. 1, can be decreased with the first method at the expense of increased Dosimetric Cost. In other words, if you lower the Segment Count, the Dosimetric Cost generally increased. The slope of the left side of the curve in FIG. 1 indicates that, initially, significant segment reduction can be achieved without a severe Dosimetric Cost penalty. FIGS. 2A-2C illustrate the tradeoff, or correlation, between Segment Count and Delivery Efficiency, and Dosimetric Cost, on a clinical treatment plan. As the Segment Count is decreased, the dose distribution becomes less conformal as the Dosimetric Cost increases. Thus, Delivery Efficiency although higher for FIG. 2C, has a poorer Dosimetric Fitness.

Figure 3:
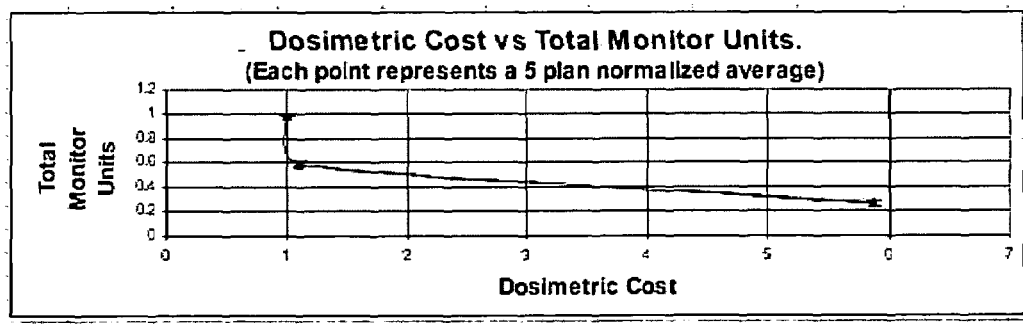
FIG. 3 is a chart illustrating the correlation between total monitor units and dosimetric cost.
Figure 4A:
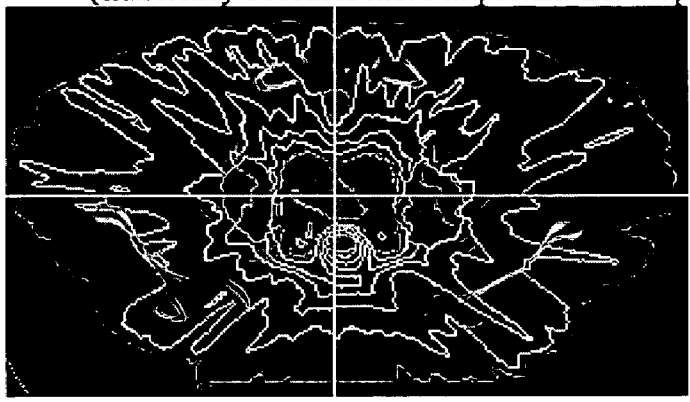
FIGS. 4A-4C are dose distribution intensity maps for three different radiotherapy plans.
Figure 4B:
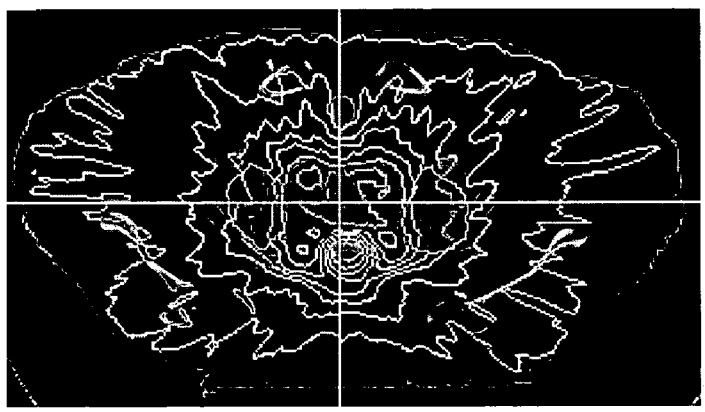
Figure 4C:
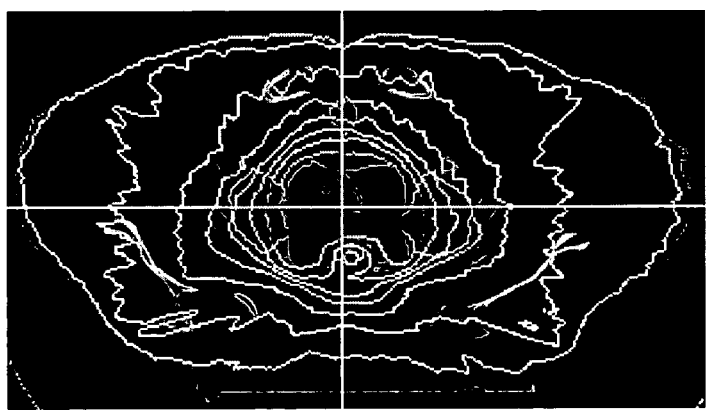

FIG. 3 illustrates the tradeoff, or correlation, between Delivery Efficiency and Dosimetric Fitness for the second method. Each point in the chart of FIG. 3 represents the average normalized Dosimetric Cost and Total Monitor Units of 5 MIMIC® treatment plans. FIG. 3 further illustrates that Total Monitor Units for a MIMIC® based MLC plan can be decreased at the expense of increased Dosimetric Cost. In other words, if you lower the number of Total Monitor Units, the Dosimetric Cost increases. The slope of the left side of the curve in FIG. 3 indicates that, initially, a significant reduction of Total. Monitor Units can be achieved without a severe dosimetric penalty, or an undesirable Dosimetric Cost. FIGS. 4A-4C illustrate the tradeoff on a clinical treatment plan. As the Total Monitor Units are decreased, as shown going from FIG. 4A to FIG. 4C, the dose distribution becomes less conformal, or desirable, as the Dosimetric Cost increases. Thus, Delivery Efficiency, although higher for FIG. 4C, has a poorer Dosimetric Fitness.

Figure 5:
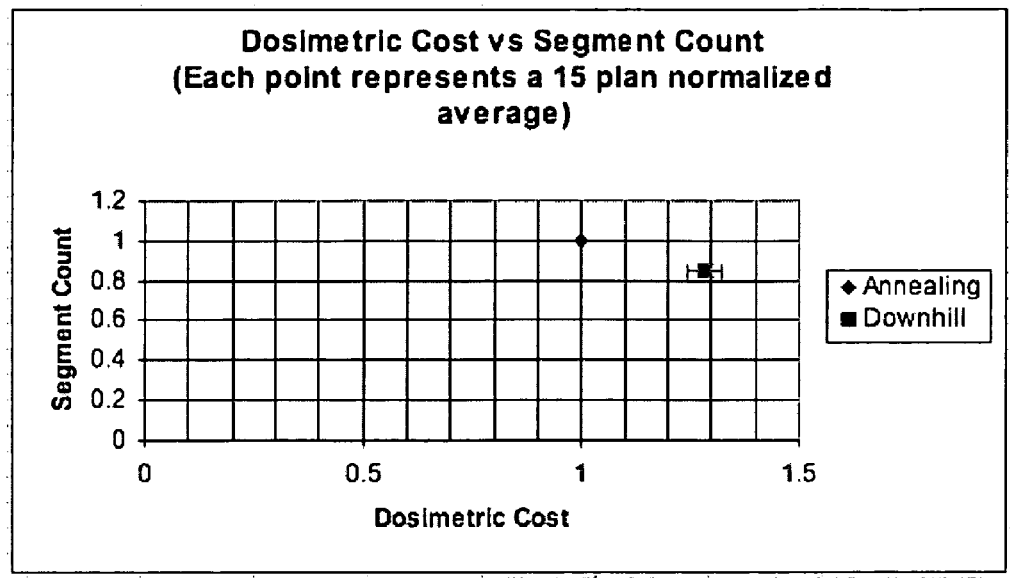
FIG. 5 is a chart illustrating the correlation between segment count and dosimetric cost.
Figure 6:
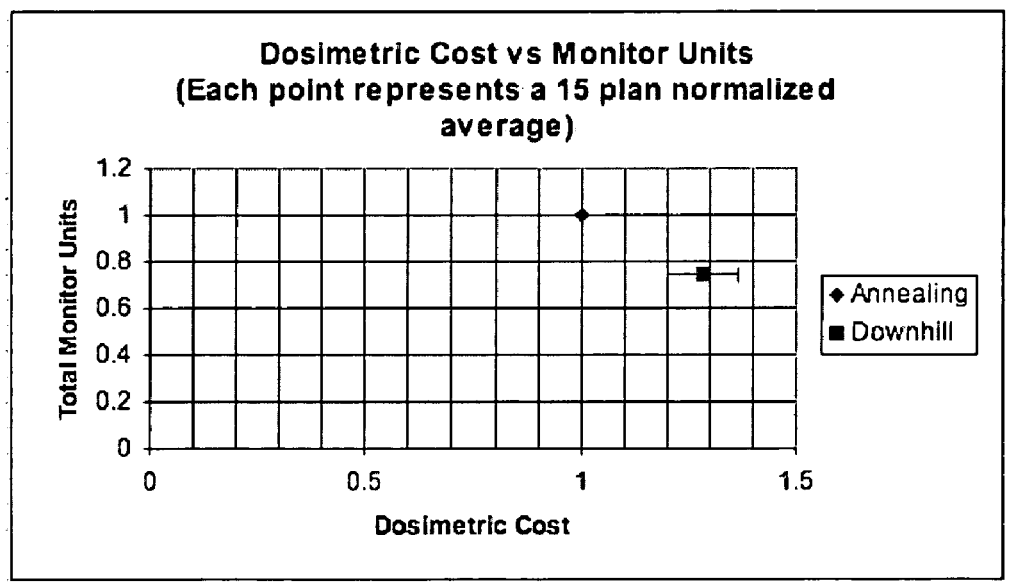
FIG. 6 is a chart illustrating the correlation between total monitor units and dosimetric cost.

FIGS. 5 and 6 illustrate the results for the third method. Each point on the charts of FIGS. 5 and 6 represents the average normalized Dosimetric Cost, Total Monitor Units, and Segment Count of 15 MLC and MIMIC® treatment plans. The charts of FIGS. 5 and 6 indicate that using simulated annealing results in plans with superior Dosimetric Cost, but higher Total Monitor Units and Segment count.

Figure 7:
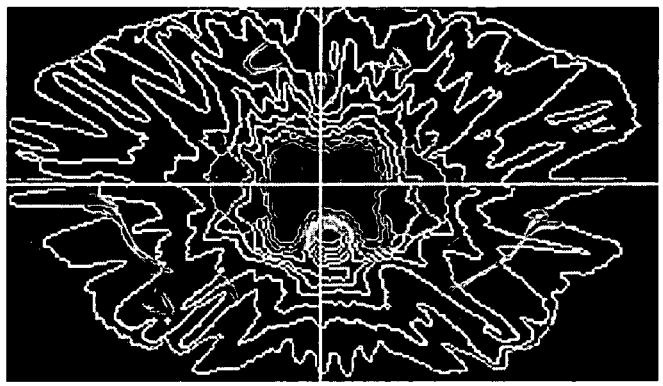
FIG. 7 is a dose distribution intensity map for a radiotherapy plan.
Figure 8:
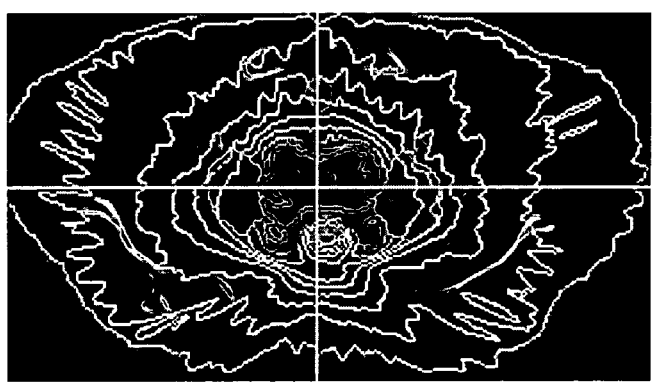
FIG. 8 is a dose distribution intensity map for a radiotherapy plan.

FIGS. 7 and 8 illustrate the tradeoff between Delivery Efficiency and Dosimetric Fitness for the third method on a clinical treatment plan. Optimizing using simulated annealing, FIG. 7 resulted in a treatment plan with lower Dosimetric Cost than optimizing with gradient descent, FIG. 8. An improved dose comes at the expense of decreased efficiency, or Delivery Efficiency. The treatment plan developed using simulated annealing (FIG. 7) requires more monitor units or a higher Total Monitor Units.

Use of the first and second described methods will enable nearly continuous control of the tradeoff, or correlation, between Delivery Efficiency and Dosimetric Fitness; and the real valued thresholds assist to enable this continuous control. The first method, wherein Segment Count is used, should be used with radiation therapy delivery systems wherein Delivery Efficiency is directly related to Segment Count. The second method, wherein Total Monitor Units is used, should be used in radiation therapy delivery systems where Delivery Efficiency is directly related to Total Monitor Units.

From the third method, wherein the selection of the optimization algorithm is used, it is seen that optimization algorithm choice can provide some control of the tradeoff between Delivery Efficiency and Dosimetric Fitness. However, the third method allows only two options, while the first two methods provide nearly continuous control of the tradeoff. Thus, although the first two methods will be generally superior for providing user control, the third method may still provide some benefit in providing user control.

Applicant incorporates by reference U.S. Pat. No. 6,038, 283, entitled "Planning Method and Apparatus for Radiation Dosimetry," issued Mar. 14, 2000, and U.S. Pat. No. 6,393, 096 B1, entitled "Planning Method and Apparatus for Radiation Dosimetry," issued May 21, 2002, which are both commonly assigned to the assignee of the present invention.

The invention claimed is:

1. A method of determining a radiation beam arrangement, the method comprising the steps of:
receiving prescription parameters for a patient target; and
evaluating a cost function for each of a set of a plurality of candidate intensity maps formed responsive to the prescription parameters to provide control of a trade-off between treatment plan delivery efficiency and dosimetric fitness within an optimizer to optimize a radiation treatment plan within a continuum between substantially optimal dosimetric fitness and enhanced delivery efficiency at an expense of dosimetric fitness, the cost function including a dosimetric cost term representing dosimetric cost and related to dosimetric fitness of the respective candidate intensity map and a delivery cost term representing delivery cost and related to delivery time to deliver radiation according to a beam arrangement represented by the respective candidate intensity map, the evaluation of the delivery cost term for each respective candidate intensity map having linear computational complexity with respect to size of the respective candidate intensity map.

2. A method as defined in claim 1, wherein the delivery cost term increases as segment count increases to deliver radiation according to a beam arrangement represented by the respective intensity map.

3. A method as defined in claim 1, wherein the delivery cost term is a function of a number of intensity changes across the respective intensity map.

4. A method as defined in claim 1, wherein the step of providing control of a trade-off between treatment plan delivery efficiency and dosimetric fitness within an optimizer includes the step of assigning a delivery cost term to each of a plurality of dose intensity maps for each proposed 5. A method as defined in claim 4,
wherein the delivery cost term is a function of a number of intensity changes across the respective dose intensity map; and
wherein the method further includes the step of rejecting each intensity map resulting in the delivery cost term exceeding a preselected threshold value.

6. A method as defined in claim 4,
wherein the delivery cost term represents a segment count; and
wherein simulated annealing is utilized to form the radiation therapy plan with a substantially optimal dosimetric cost and a delivery cost not exceeding a predetermined segment count.

7. A method as defined in claim 2, wherein the delivery cost term is a function of total monitor units to deliver radiation according to a beam arrangement represented by the respective intensity map.

8. A method as defined in claim 1,
wherein delivery efficiency is represented by total monitor units to deliver the radiation treatment plan; and
wherein the step of providing control of a trade-off between treatment plan delivery efficiency and dosimetric fitness within an optimizer includes the step of limiting inflation of total monitor units from initially simple and efficient beam arrangements to more complex beam arrangements.

9. A method as defined in claim 8,
wherein delivery efficiency is represented by total monitor units to deliver the radiation treatment plan;
wherein the step of providing control of a trade-off between treatment plan delivery efficiency and dosimetric fitness within an optimizer includes the step of assigning a delivery cost term to each of a plurality of dose intensity maps for each proposed radiation therapy treatment plan, the delivery cost term indicating total monitor units associated with each respective intensity map; and
wherein the method further includes the step of rejecting each intensity map resulting in the delivery cost term exceeding a preselected threshold value.

10. A method as defined in claim 8, wherein simulated annealing is utilized to form the radiation therapy plan with a substantially optimal dosimetric cost and a delivery cost not exceeding a predetermined total monitor units.

11. A method of providing control of a trade-off between treatment plan delivery efficiency and dosimetric fitness to optimize a radiation treatment plan within a continuum between delivery efficiency and dosimetric fitness, the method comprising the steps of:
applying prescription parameters to each of a plurality of optimization algorithms within an optimizer, the plurality of optimization algorithms including a local optimization algorithm and a global optimization algorithm, the local optimization algorithm providing greater delivery efficiency than that of the global optimization algorithm, the global optimization algorithm providing greater dosimetric fitness than the local optimization algorithm; and
selecting one of the plurality of algorithms to be the optimizer responsive to a user selection between enhanced delivery efficiency and enhanced dosimetric fitness.

12. A method as defined in claim 11, wherein the global optimization algorithm is a simulated annealing algorithm, and wherein the local optimization algorithm is a gradient descent algorithm.

13. A method of providing control of a trade-off between treatment plan delivery efficiency and dosimetric fitness to optimize a radiation treatment plan within a continuum between delivery efficiency and dosimetric fitness, the method comprising the steps of:
assigning a delivery cost term within an optimizer to each of a plurality of intensity maps representing a potential radiation beam arrangement, the assignment based on complexity of each respective intensity map; and
evaluating an objective cost function for each of the plurality of intensity maps, the objective function including a dosimetric cost term and the delivery cost term, the dosimetric cost term representing dosimetric fitness of the respective intensity map and the delivery cost term representing delivery efficiency.

14. A method as defined in claim 13, wherein the delivery cost term is a function of delivery time required to deliver radiation according to a beam arrangement represented by the respective intensity map.

15. A method as defined in claim 13, wherein the delivery cost term represents at least one of the following: a segment count and an amount of total monitor units, to deliver radiation according to a beam arrangement represented by the respective intensity map.

16. A method as defined in claim 13,
wherein the delivery cost term is a function of a number of intensity changes across the respective dose intensity map; and
wherein the method further includes the step of rejecting each intensity map resulting in the delivery cost term exceeding a preselected threshold value.

17. A method as defined in claim 13,
wherein the delivery cost term represents a segment count; and
wherein simulated annealing is utilized to form the radiation therapy plan having a delivery cost not exceeding a predetermined segment count and having a minimal dosimetric cost.

18. A method as defined in claim 13,
wherein the delivery cost term represents total monitor units to deliver the radiation treatment plan; and
wherein the step of evaluating the objective function includes the step of limiting inflation of total monitor units from initially simple and efficient beam arrangements to more complex beam arrangements.

19. A method of providing control of a trade-off between treatment plan delivery efficiency and dosimetric fitness to optimize a radiation treatment plan within a continuum between delivery efficiency and dosimetric fitness, the method comprising the steps of:
evaluating an objective cost function within an optimizer for each of a plurality of intensity maps, the objective function including a dosimetric cost term and the delivery cost term, the delivery cost term representing total monitor units to deliver radiation according to a beam arrangement represented by the respective intensity map; and
rejecting each intensity map resulting in the delivery cost term exceeding a preselected threshold value.

20. A method as defined in claim 19, wherein simulated annealing is utilized to form the radiation therapy plan with substantially optimal dosimetric cost and a delivery cost not exceeding a predetermined total monitor units.

* * * * *